United States Patent
Kato et al.

(10) Patent No.: US 8,664,405 B2
(45) Date of Patent: Mar. 4, 2014

(54) SULFONIC ACID SALT COMPOUND OF 4-CARBAMOYL-5-HYDROXY-IMIDAZOLE DERIVATIVE

(75) Inventors: Nobuo Kato, Suita (JP); Yusuke Higuchi, Suita (JP); Chihiro Kondo, Suita (JP); Makoto Sunagawa, Itami (JP)

(73) Assignee: Fujifilm Corporation, Tokyo (JP)

( * ) Notice: Subject to any disclaimer, the term of this patent is extended or adjusted under 35 U.S.C. 154(b) by 163 days.

(21) Appl. No.: 12/733,656

(22) PCT Filed: Sep. 16, 2008

(86) PCT No.: PCT/JP2008/067050
§ 371 (c)(1),
(2), (4) Date: Mar. 12, 2010

(87) PCT Pub. No.: WO2009/035168
PCT Pub. Date: Mar. 19, 2009

(65) Prior Publication Data
US 2010/0210855 A1    Aug. 19, 2010

(30) Foreign Application Priority Data
Sep. 14, 2007   (JP) .................... 2007-238653
Feb. 8, 2008    (JP) .................... 2008-028268

(51) Int. Cl.
*C07D 233/90* (2006.01)
*C07C 233/62* (2006.01)

(52) U.S. Cl.
USPC ...................... 548/323.1; 564/160

(58) Field of Classification Search
USPC ...................... 548/316.4; 514/386
See application file for complete search history.

(56) References Cited

FOREIGN PATENT DOCUMENTS

| CA | 1 235 065 | 4/1988 | | |
|---|---|---|---|---|
| DE | 27 40 281 | 3/1978 | | |
| JP | 52-118468 | 10/1977 | | |
| JP | 58-24569 | 2/1983 | | |
| JP | 58-35115 A | * 3/1983 | ........... | A61K 31/415 |
| JP | 2000-11753 | 1/2000 | | |

OTHER PUBLICATIONS

Bastin et al, Organic Process Research & Development, 2000, 4, pp. 427-435.*
Stahl et al, Handbook of Pharmaceutical Salts, Chapter 12, pp. 265-327.*
Supplementary European Search Report issued Oct. 26, 2011 in corresponding European Application No. 08 83 0235.
International Search Report issued Dec. 16, 2008 in corresponding International Application No. PCT/JP2008/067050, of record.
International Preliminary Report on Patentability and Written Opinion of the International Searching Authority, issued Apr. 15, 2010, in PCT/JP2008/067050.
Hiroyuki Ono et al., "Ion-sei Ekitai-Kaihatsu no Saizensen to Mirai-", Feb. 1, 2003, pp. 18-24.
Chongwei Yue et al., "Syntheses of 4-carbamoylimidazole-5-hydroxyl substituted α-methylcinnamates", Youji Huaxue, 1986, vol. 6, pp. 443-446.

* cited by examiner

*Primary Examiner* — Alicia L Otton
(74) *Attorney, Agent, or Firm* — Wenderoth, Lind & Ponack, L.L.P.

(57) ABSTRACT

The object is to provide a stable SM-108 derivative, which is effective as a carcinostatic agent, particularly an SM-108 derivative having good storage stability. An SM-108 compound having good storage stability can be produced by producing an organic sulfonic acid salt compound of SM-108. Further, a crystalline SM-108 compound containing a trace amount of an organic carboxylic acid can be produced by using an aqueous solution of the organic sulfonic acid salt of SM-108, and by adding an alkali metal salt of an organic carboxylic acid to the aqueous solution to neutralize the aqueous solution and then causing the crystal precipitation in the solution.

15 Claims, 2 Drawing Sheets

SULFONIC ACID SALT COMPOUND OF 4-CARBAMOYL-5-HYDROXY-IMIDAZOLE DERIVATIVE

TECHNICAL FIELD

The present invention relates to derivatives of 4-carbamoyl-5-hydroxyimidazole. In more detail, the present invention relates to sulfonic acid salts of 4-carbamoyl-5-hydroxyimidazole, which have good storage stability, and preparation thereof.

BACKGROUND ART

4-Carbamoy-5-hydroxyimidazol (SM-108; [2]) is a known compound, a synthetic method of which is described in J. Am. Chem. Soc., 74, 2892 (1952), and has been known to have potent antitumor activities as described in JP S53-32124 A. The clinical trial of SM-108 had been conducted by Sumitomo Pharmaceuticals Co., Ltd. in 1980s.

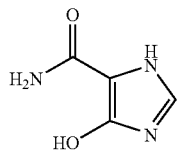

[2]

The clinical outcomes clearly revealed that SM-108 shows excellent effects against myelodysplastic syndrome (MDS) and chronic myelocytic leukemia (CML) with reduced side effects such as myelosuppression action. However, the development of SM-108 as a chemotherapeutic agent was discontinued partly because of its chemical instability. SM-108 tends to produce a blue colorant by the air-oxidation. Although the drug formulation to improve the storage stability of SM-108 had been attempted by adding antioxidant agents as described in JP S58-35115 A, those efforts are far from the ideal method to overcome the problem efficiently.

On the other hand, MDS, the main target disorder of SM-108, is still categorized in a poor-prognotic syndrome and the number of patients is increasing gradually, especially in Europe and the United States. However, there is no efficacious therapeutics yet. Under these circumstances, the development of a new SM-108 derivative, which has improved storage stability, has been strongly desired.

DISCLOSURE OF THE INVENTION

The object of this invention is to provide a stable SM-108 derivative, which is effective as an anticancer agent, particularly to provide an SM-108 derivative having good storage stability.

The patent literature, JP S53-32124 A, describes that SM-108 is a low toxic and orally administrative anticancer drug. 4-Carbamoyl-5-hydroxyimidazole (SM-108) itself can be used in oral administration, and its alkali metal salts, such as a sodium salt, can be used as injections.

The present inventors have intensively studied to provide 4-carbamoyl-5-hydroxyimidazole derivatives, which are highly stable against air-oxidation conditions and can be used as orally administrable drugs in place of SM-108. As a result of keen investigations, the inventors found that organic sulfonic acid salts of SM-108 are highly stable and orally administrable.

Moreover, the neutralization of sulfonates of SM-108 having excellent storage stability could provide highly-pure SM-108. However, pure SM-108 obtained by complete neutralization with alkali metal solution, such as aqueous sodium hydroxide, had poor storage stability. As described in patent document, JP S60-185727 A, the stability of SM-108 is enhanced by coexistence with an acid of which pKa is less than 4. However, in conventional procedures, since it was always necessary to pass through free SM-108, sufficient stability could not be obtained.

Since, in the new synthetic procedures described above, sulfonates of SM-108 having good storage stability can be provided directly, neutralization was carried out by adding an alkaline metallic salt of a weak acid to the sulfonates. The inventors found out that a crystalline compound of SM-108 containing a small amount of an acid homogenously could be obtained without passing through free SM-108 by adjusting an amount of the alkaline metallic salt of a weak acid in the neutralization. SM-108 provided by this method has completely different characteristics from heretofore known SM-108 especially in its storage stability. On the base of these findings described above, the inventors accomplished the present invention.

SUMMARY OF THE INVENTION

The present invention relates to:
(1) a sulfonic acid salt of imidazole derivative having the following general formula [1]:

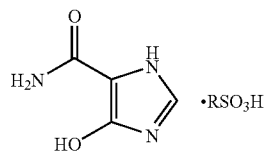

[1]

wherein R is a substituted or unsubstituted alkyl group, or a substituted or unsubstituted aryl group,
(2) the sulfonic acid salt according to (1) above, wherein the substituted or unsubstituted alkyl group is a $C_1$ to $C_6$ lower alkyl group, or a $C_5$ to $C_{10}$ alicyclic alkyl group,
(3) the sulfonic acid salt according to (1) above, wherein the substituted or unsubstituted aryl group is a $C_6$ to $C_{10}$ aromatic aryl group,
(4) the sulfonic acid salt according to (1) or (2) above, wherein the substituted or unsubstituted alkyl group is a methyl, ethyl, trifluoromethyl, menthyl group,
(5) the salt according to (1) or (3) above, wherein the substituted or unsubstituted aryl group is a phenyl, p-methylphenyl group,
(6) a pharmaceutical composition for oral administration comprising the sulfonic acid salt of imidazole derivative according to (1) as an active ingredient,
(7) the pharmaceutical composition for oral administration according to (7), wherein the substituted or unsubstituted alkyl group is a methyl, ethyl, trifluoromethyl, menthyl group,
(8) a crystalline compound of a methanesulfonic acid salt of 4-carbamoyl-5-hydroxy-imidazole,
(9) a crystalline compound of an ethanesulfonic acid salt of 4-carbamoyl-5-hydroxy-imidazole,
(10) a crystalline compound of a camphorsulfonic acid salt of 4-carbamoyl-5-hydroxy-imidazole,

(11) a crystalline compound of a p-toluenesulfonic acid salt of 4-carbamoyl-5-hydroxy-imidazole,
(12) a crystalline compound of a benzenesulfonic acid salt of 4-carbamoyl-5-hydroxy-imidazole,
(13) a crystalline compound of a hydrochloric acid salt of 4-carbamoyl-5-hydroxy-imidazole.
(14) a method for preparing an organic sulfonic acid salt of aminomalonamide by direct recrystallization performed in an alcoholic solvent with the addition of the organic sulfonic acid into a crude product obtained through the reaction of diethyl aminomalonate and ammonia in an organic solvent,
(15) the method for preparation according to (14) above, wherein the organic solvent is an alcoholic solvent,
(16) the method for preparation according to (14) or (15) above, wherein the alcoholic solvent is methyl alcohol,
(17) the method for preparation according to any of (14) to (16) above, wherein the organic sulfonic acid is an aryl sulfonic acid,
(18) the method for preparation according to any of (14) to (17) above, wherein the aryl sulfonic acid is benzenesulfonic acid, toluenesulfonic acid,
(19) a method for preparing an organic sulfonic acid salt of SM-108 characterized in obtaining the organic sulfonic acid salt of SM-108 precipitated out after an organic sulfonic acid salt of aminomalonamide is added to trialkoxymethine stirred in an organic solvent under heating,
(20) the method for preparation according to (17) above, wherein the organic sulfonic acid is an arylsulfonic acid,
(21) the method for preparation according to (17) or (18) above wherein the arylsulfonic acid is benzenesulfonic acid, toluenesulfonic acid,
(22) the method for preparation according to any of (19) to (21) above, wherein the organic solvent is an alcoholic solvent,
(23) the method for preparation according to (19) or (22) above, wherein the alcoholic solvent is ethyl alcohol,
(24) a method for preparing an organic sulfonic acid salt of SM-108 characterized in obtaining the organic sulfonic acid salt of SM-108 precipitated out after an organic sulfonic acid salt of aminomalonamide and trialkoxymethine are mixed in an organic solvent stirred under heating, wherein the organic sulfonic acid salt of aminomalonamide is obtained by the addition of ammonia and an organic sulfonic acid to an inorganic acid salt of diethyl aminomalonate stirred under heating in an organic solvent under atmosphere of an inert gas.
(25) the method for preparing an organic sulfonic acid salt of SM-108 according to (24) above, wherein the organic sulfonic acid is an arylsulfonic acid,
(26) the method for preparation according to (24) or (25) above, wherein the arylsulfonic acid is benzenesulfonic acid, toluenesulfonic acid,
(27) the method for preparation according to any of (24) to (26) above, wherein the organic solvent is an alcoholic solvent,
(28) the method for preparation according to (24) to (27) above, wherein the alcoholic solvent is ethyl alcohol,
(29) a method for preparing SM-108 characterized in collecting a crystalline compound of SM-108 precipitated out by dilution of an aqueous solution with a hydrophilic organic solvent, wherein the aqueous solution is obtained after neutralization of an organic sulfonic acid salt of SM-108 in an aqueous solution by the addition of an alkaline metallic salt of an organic carboxylic acid or an aqueous solution thereof,
(30) the method for preparation of SM-108 according to (29) above, wherein the alkaline metallic salt of an organic carboxylic acid is a sodium salt of arylcarboxylic acid,
(31) the method for preparation according to (29) or (30) above, wherein 0.93 to 1.0 mole equivalent of the alkaline metallic salt of the organic carboxylic acid is used for the neutralization of the organic sulfonic acid salt of SM-108,
(32) the method for preparation according to any of (29) to (31) above, wherein the arylcarboxylic acid is benzoic acid,
(33) the method for preparation of SM-108 according to any of (29) to (32) above, wherein the organic sulfonic acid is benzenesulfonic acid, toluenesulfonic acid,
(34) the method for preparation of SM-108 according to any of (29) to (33) above, wherein the hydrophilic organic solvent is acetone,
(35) a crystalline compound of SM-108 having a good storage stability, characterized in containing 0.05~5% of an organic carboxylic acid remained prepared by the method according to (29) above,
(36) the crystalline compound of SM-108 having a good storage stability according to (35) above, wherein the organic carboxylic acid is benzoic acid, and
(37) the crystalline compound of SM-108 having a good storage stability according to (35) or (36) above, containing 0.1 to 3% of an organic carboxylic acid remained.

According to the present invention, it becomes possible to provide an organic sulfonic acid salt of 4-carbamoyl-5-hydroxyimidazole which is orally-available and has improved oxidation stability, or a crystalline compound of SM-108 having good storage stability. Thus, it becomes possible to provide an orally-available agent for leukemia, especially for MDS.

BEST MODE FOR CARRYING OUT THE INVENTION

—The First Aspect—

Figure 1:
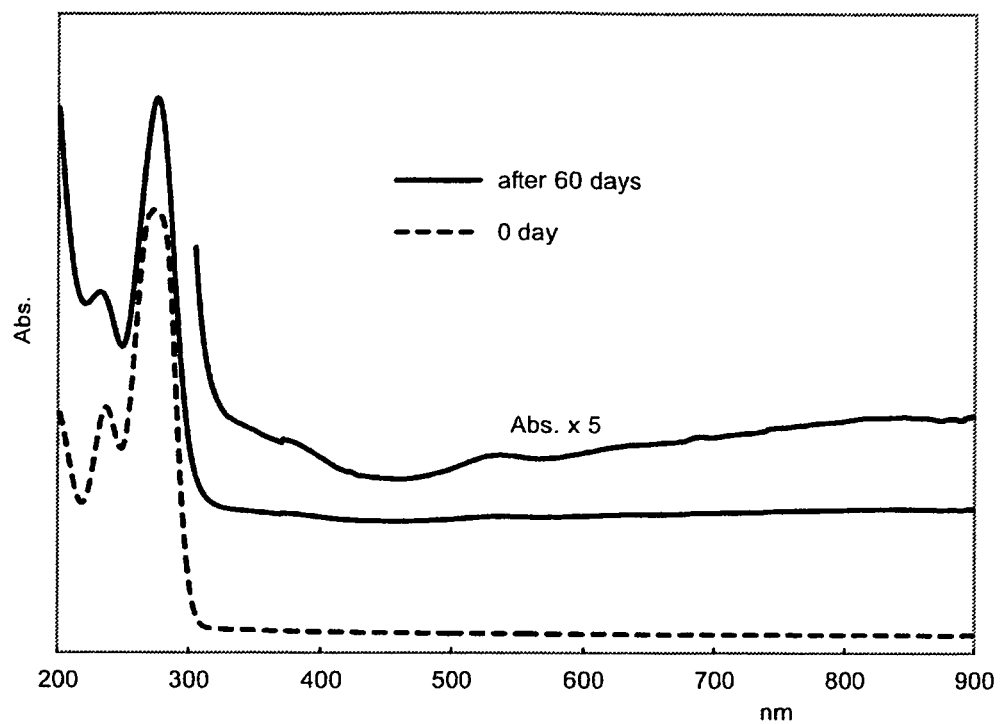
FIG. 1 shows UV-Vis spectra change of an aqueous solution of SM-108 over time.
Figure 2:
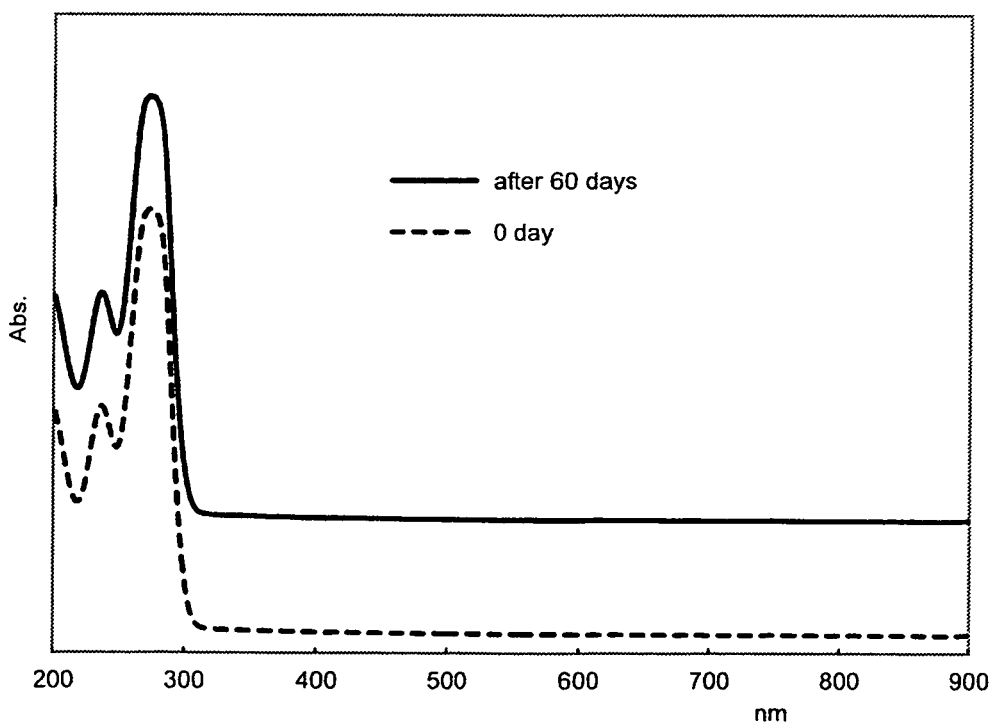
FIG. 2 shows UV-Vis spectra change of an aqueous solution of a hydrochrolic acid salt of SM-108 over time.

The first aspect of the invention relates to an organic sulfonic acid salt of SM-108. Various terms and preferable examples referred to the present specification are explained as follows.

"Unsubstituted or a substituted alkyl" is a $C_1$ to $C_6$ alkyl group that includes, for example, methyl, ethyl, n-propyl, i-propyl, n-butyl, n-hexyl, trifluoromethyl, trifluoroethyl, 2-hydroxyethyl group, or a $C_5$ to $C_{10}$ alicyclic alkyl group that includes, for example, cyclohexyl, menthyl group. Among them, a methyl, ethyl, trifluoromethyl, or menthyl group is especially preferable. The substituent in "substituted alkyl" is a halogen atom such as a fluorine or chlorine atom, an alkoxy group such as a methoxy or ethoxy group, or a $C_1$ to $C_4$ alkyl group such as a methyl or ethyl group.

"Unsubstituted or a substituted aryl" is $C_6$ to $C_{10}$ unsubstituted aryl or substituted aryl, for example, a p-methylphenyl or naphthyl group. Among them, phenyl or p-methylphenyl is especially preferable. The substituent in "substituted aryl" is a halogen atom such as a fluorine or chlorine atom, an alkoxy group such as a methoxy or ethoxy group, or a $C_1$ to $C_4$ alkyl group such as a methyl or ethyl group.

Among a sulfonic acid salt in this invention, a methanesulfonic acid salt, an ethanesulfonic acid salt, a camphorsulfonic acid salt, p-toluenesulfonic acid salt, or benzensulfonic acid salt is especially favorable. These sulfonic acid salts can be obtained as colorless crystalline compounds having good storage stability.

A sulfonic acid salt in this invention can be prepared by the method described in J. Am. Chem. Soc., 74, 2892 (1952) or in JP S53-32124 A. However, it can be provided more efficiently by the following two successive reactions:

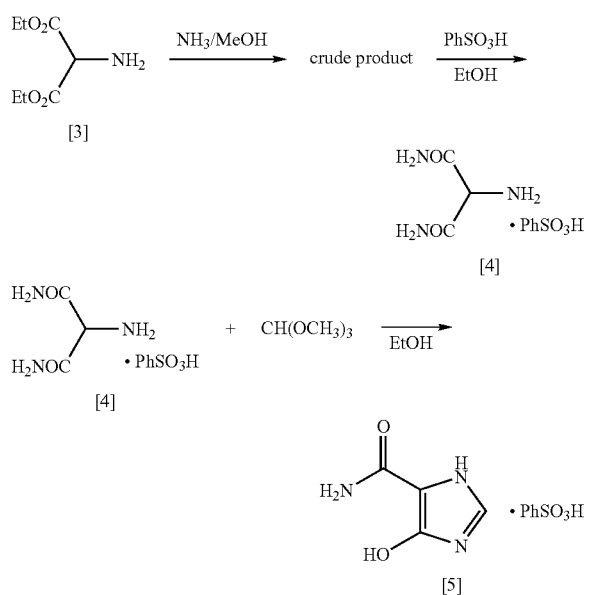

—The Second Aspect—

The second aspect of the invention relates to a synthetic procedure of an organic sulfonic acid salt of SM-108.

"An organic sulfonic acid" in this invention is a sulfonic acid of which substituent is a $C_1$ to $C_6$ unsubstituted or substituted alkyl group, a $C_5$ to $C_{10}$ alicyclic alkyl group, or an unsubstituted or substituted aryl group. A $C_1$ to $C_6$ unsubstituted or substituted alkyl group, a $C_5$ to $C_{10}$ alicyclic alkyl group, and an unsubstituted or substituted aryl group here means the same with those defined in the section of "THE FIRST ASPECT". Among them, methanesulfonic acid, ethanesulfonic acid, trifluoromethanesulfonic acid, p-toluenesulfonic acid, or benzenesulfonic acid is especially favorable.

"An organic solvent" in this invention is a solvent that is used for promoting the reactions by dissolving reactants and reagents. Any kind of solvent can be used if they do not affect the reactions; for example, an alcoholic solvent such as methanol or ethanol, or a non-alcoholic solvent such as toluene, benzene, dichloromethane, chloroform, tetrahydrofuran, or dioxane can be used. Moreover, combined use of these solvents is also applicable. Among them, methanol or ethanol is especially favorable.

"An inert gas" in this invention is a gas that is used in the reaction for the purpose of excluding atmospheric oxygen and moisture from the reaction atmosphere, such as nitrogen or argon gas.

"A trialkoxymethine" in this invention is a methane substituted by a $C_1$ to $C_4$ alkoxy group such as trimethoxymethine, triethoxymethine, tri-n-propoxymethine, or tri-i-propoxymethine. Among them, trimethoxymethine is especially preferable.

—The Third Aspect—

The third aspect of the invention relates to a crystalline compound of SM-108. "An organic carboxylic acid" in this invention is a substituted or unsubstituted $C_2$ to $C_{20}$ alkanoic acid such as acetic acid, propionic acid, hexanoic acid, lactic acid, citric acid, malic acid, or a substituted or unsubstituted $C_8$ to $C_{12}$ aralkanoic acid such as mandelic acid, benzilic acid, or a substituted or unsubstituted $C_7$ to $C_{12}$ arylcarboxlic acid such as benzoic acid, p-methylbenzoic acid, salicylic acid, p-hydroxybenzoic acid. Among them, a crystalline organic carboxylic acid such as lactic acid, citric acid, manedelic acid, malic acid, or benzoic acid is especially preferable.

The remaining amount of carboxylic acid is in the range of 0.05~5%, and varies depending on pKa of the carboxylic acid. When benzoic acid, which pKa is 4.21, is used, the remaining amount of the acid is around 2.5%. The remaining amount of the organic carboxylic acid tends to be increased as its acidity is stronger, whereas the remaining amount tends to be decreased as the acidity is weaker. The range of ca. 0.1 to 3% as the remaining amount of an organic carboxylic acid is especially favorable.

—The Fourth Aspect—

The fourth aspect of the invention relates to a method for preparing a crystalline compound of SM-108.

"An alkali metal salt" in this invention is a lithium salt, sodium salt, or potassium salt. Among them, a sodium salt is especially favorable.

The amount of an alkali metal salt of an organic carboxylic acid used in this invention can be an equimolar to an organic sulfonic acid salt of SM-108, or slightly less than that. As SM-108 oxidized easily in basic conditions, it is preferable to keep acidic in the neutralization step. As an example, it is desirable to use 0.93 to 1.0 equivalent of an alkali metal salt of an organic carboxylic acid for an organic sulfonic acid salt of SM-108.

"A hydrophilic organic solvent" of this invention is an organic solvent that can be soluble homogeneously with water such as acetone, tetrahydrofuran, methanol, or ethanol. Preferably acetone is exemplified. The other terms are the same with those already defined earlier.

An organic sulfonic acid salt of SM-108 or a crystalline compound of SM-108 described in the present invention can be used as an agent orally- or parenterally-available (for example, intravenously, intramuscularly, or rectally). Orally-available forms include, for example, a tablet, a capsule, a pill, granules, powders, liquid, syrup, suspension etc. Parenterally-available forms are, for example, an aqueous or oily solution for injection, an ointment, a cream, a lotion, an aerosol, a suppository, a plaster, etc. The suitable administration forms as mentioned above may be prepared in a conventional manner by mixing with a pharmaceutically acceptable carrier, excipient, binder, stabilizer, etc. When administered in the form of injection, a pharmaceutically acceptable buffering agent, a solubilizer, an isotonic agent, etc. may be added thereto.

The dosage and the frequency of the administration of the mendicant described in the present invention vary according to the symptoms, ages, body weights, the administration forms, etc., but it is usually in the range of 50 to 500 mg per day with all at once or divided into several times of administration.

The prevent invention is explained by illustrating in the following Examples, which are not intended to limit the invention thereto. It is possible to modify procedures practically according to the principle of the present invention described above or below. Such technical modifications are also covered by the present invention.

Example 1

Synthesis of SM-108 [2]

(1) Neutralization of hydrochloric acid salt of diethyl 2-aminomalonate

A saturated aqueous solution of sodium hydrogencarbonate (100 ml) and hydrochloric acid salt of diethyl 2-aminomalonate (10.0 g; 47.3 mmol) were added to dichloromethane (100 ml) and stirred. The aqueous layer was extracted with dichloromethane and the organic phase was washed with brine. The organic phase was separated and dried over anhydrous magnesium sulfate. After filtration, the filtrate was collected and the solvent was removed under reduced pressure to give diethyl 2-aminomalonate [3] (8.16 g; 46.6 mmol; yield 99%) as a colorless oil.

$^1$H-NMR (400 MHz, CDCl$_3$): δ 4.31 (5H, m), 1.89 (3H, s), 1.31-1.26 (6H, m).

(2) Synthesis of 2-aminomalonamide

To diethyl 2-aminomalonate [3] (8.16 g; 46.6 mmol) prepared above, 2 M ammonia in methanol (233 ml; 466 mmol) was added and heated at 60° C. for 19 hours under an argon atmosphere. The reaction solvent was removed under reduced pressure to give crude 2-aminomalonamide as pale yellow powders. The yellow colored impurities were removed by solid-liquid extraction with methanol (100 ml) by use of a Soxhlet extractor at 90° C. for 21 hours under an argon atmosphere. The nearly colorless residue in the extraction thimble was recrystallized from water to give colorless 2-aminomalonamide (2.65 g; 22.6 mmol; yield 49%).

$^1$H-NMR (400 MHz, DMSO-d$_6$): δ 7.38 (2H, brs), 7.23 (2H, brs), 3.73. (1H, s), 2.13 (2H, s).

$^{13}$C-NMR (100 MHz, DMSO-d$_6$): δ 172.0 (2C), 58.2 (1C).

melting point: 192° C.

(3) Synthesis of SM-108 [3]

2-Aminomalonamide (99.2 mg; 0.847 mmol), formamidine acetate (88.6 mg; 0.851 mmol), and formic acid (128 μl) were dissolved into dry ethanol (3.8 ml) and were introduced into a sealed tube. The air in the tube was evacuated, sealed, and then heated at 80° C. for 1 hour. After opening the tube, into the reaction mixture was added a small portion of formic acid, and then the volatiles were removed in vacuo azeotropically with toluene. The resulting light blue solid was filtered and washed with small amount of cold water. The powder obtained was dissolved in formic acid again and the solvent removed in vacuo with toluene to give nearly white SM-108 (65.5 mg; 0.515 mmol).

$^1$H-NMR (400 MHz, DMSO-d$_6$): δ 7.83 (1H, s), 7.03 (1H, brs), 6.64 (1H, brs).

$^{13}$C-NMR (100 MHz, DMSO-d$_6$): δ 161.9 (1C), 156.5 (1C), 125.8 (1C), 99.6 (1C).

melting point: 185.7° C.

Example 2

Synthesis of benzenesulfonic acid salt of SM-108 [5]

To SM-108 (165.5 mg; 0.515 mmol) obtained in Example 1, benzenesulfonic acid monohydrate (331 mg; 1.88 mmol) was added and dissolved in a small amount of water. Toluene was added and the volatiles were evaporated azeotropically under reduced pressure. The residue was washed with ethyl acetate to give benzensulfonic acid salt of SM-108 [5] (109.8 mg; 0.362 mmol; yield 43%) as colorless fine scales.

$^1$H-NMR (400 MHz, DMSO-d$_6$): δ 8.24 (1H, brs), 7.58 (2H, m), 7.33-7.28 (3H, m).

melting point: 238.2° C. (decomposition).

Example 3

Synthesis of organic sulfonic acid salts of SM-108 [1] and related compounds

By use of SM-108 (127 mg; 1.00 mmol) obtained in Example 1 and methanesulfonic acid (101 mg; 1.05 mmol), methanesufonic acid salt of SM-108 was synthesized according to the procedure described in Example 2.

Organic sulfonic acid salts and a hydrochloric acid salt of SM-108 shown in Table 1 were prepared similarly.

TABLE 1

| Salts of SM-108 | Melting point | NMR (400 MHz, DMSO-d6) δ (ppm) |
|---|---|---|
| Methanesulfonic acid salt | 198.2° C. (decomposition) | 8.46 (1H, brm), 2.37 (3H, s) |
| Ethanesulfonic acid salt | 208.0° C. (decomposition) | 8.29 (1H, brm), 2.41 (2H, q, J = 7 Hz), 1.06 (3H, t, J = 7 Hz) |
| Camphorsulfonic acid salt | 213.9° C. (decomposition) | 8.29 (1H, brm), 2.87 (1H, d, J = 14.8 Hz), 2.66 (1H, m), 2.58 (1H, d, J = 14.8 Hz), 2.23 (1H, dm, J = 18.2 Hz), 1.92 (1H, brt, J = 4 Hz), 1.84 (1H, m), 1.79 (1H, d, J = 18.2 Hz), 1.26 (2H, m), 1.03 (3H, s), 0.73 (3H, s) |
| p-Toluenesulfonic acid salt | 252.9° C. (decomposition) | 8.22 (1H, brm), 7.46 (2H, dm, J = 8 Hz), 7.10 (2H, dm, J = 8 Hz), 2.28 (3H, s) |
| Hydrochloric acid salt | 238.0° C. (decomposition) | 8.29 (1H, brm) |

Example 4

The Alternative Synthetic Procedure of SM-108 [2]

(1) Synthesis of benzenesulfonic acid salt of 2-aminomalonamide [4]

To diethyl 2-aminomalonate (16.5 g; 94.4 mmol) prepared according to Example 1, 7 M ammonia in methanol (94 ml; 658 mmol) was added and heated at 55° C. for 24 hours under an argon atmosphere. Evaporation of the solvent under reduced pressure left a pale yellow residue, to which benzenesulfonic acid monohydrate 16.3 g (92.6 mmol) was added and recrystallized from ethanol (2.0 l) to give a colorless crystalline compound. Repetition of recrystallization afforded benzenesulfonic acid salt of 2-aminomalonamide [4] (21.4 g; 77.7 mmol; yield 82%) as colorless scales.

$^1$H-NMR (400 MHz, DMSO-$d_6$): δ 8.23 (3H, s), 7.86 (2H, s), 7.71 (2H, s), 7.58 (2H, m). 7.30 (3H, m), 4.40 (1H, s).

$^{13}$C-NMR (100 MHz, DMSO-$d_6$): δ 164.8 (2C), 128.4 (1C), 127.6 (2C), 125.4 (2C), 55.2 (1C).

melting point: 223.7-224.1° C.

(2) Synthesis of benzenesulfonic acid salt of SM-108 [5]

Into a suspension of benzenesulfonic acid salt of 2-aminomalonamide [4] (1.20 g; 4.37 mmol) prepared above and benzenesulfonic acid monohydrate (81 mg; 0.46 mmol) in dry ethanol (100 ml) was added trimethyl orthoformate (1.9 ml; 17.4 mmol), and was refluxed for 2 hours under an argon atmosphere. The resulting white suspension was stirred overnight at room temperature and the precipitates were collected by filtration to give colorless benzenesulfonic acid salt of SM-108 (1.02 g; 3.58 mmol; yield 82%), which was identical with that obtained in Example 2.

(3) Synthesis of SM-108 [2]

Benzene sulfonic acid salt of SM-108 (500 mg; 1.75 mmol) was dissolved into hot water (5 ml). The resulting solution was neutralized with sodium hydrogencarbonate (147 mg; 1.75 mmol) and acetone (40 ml) was added. After stirring, the precipitated colorless crystals were collected by filtration and were dried in vacuo to give SM-108 [2] (218 mg; 1.72 mmol; yield 98%) as colorless powders.

Example 5

The alternative synthetic procedure of benzenesulfonic acid salt of 2-aminomalonamide [4]

Into hydrochloric acid salt of diethyl 2-aminomalonate [3] (21.2 g; 100 mmol) were added 7 M ammonia in methanol (100 ml) and benzenesulfonic acid monohydrate (17.6 g; 100 mmol), and heated to reflux for 24 hours under an argon atmosphere. After evaporating off the solvent under reduced pressure, the resulting residue was recrystallized from ethanol (2.0 l). The deposited crystals were collected by filtration and repetition of recrystallization afforded benzenesulfonic acid salt of 2-aminomalonamide [4] as colorless scales.

Example 6

Synthesis of Crystalline Compound of SM-108

Figure 3:
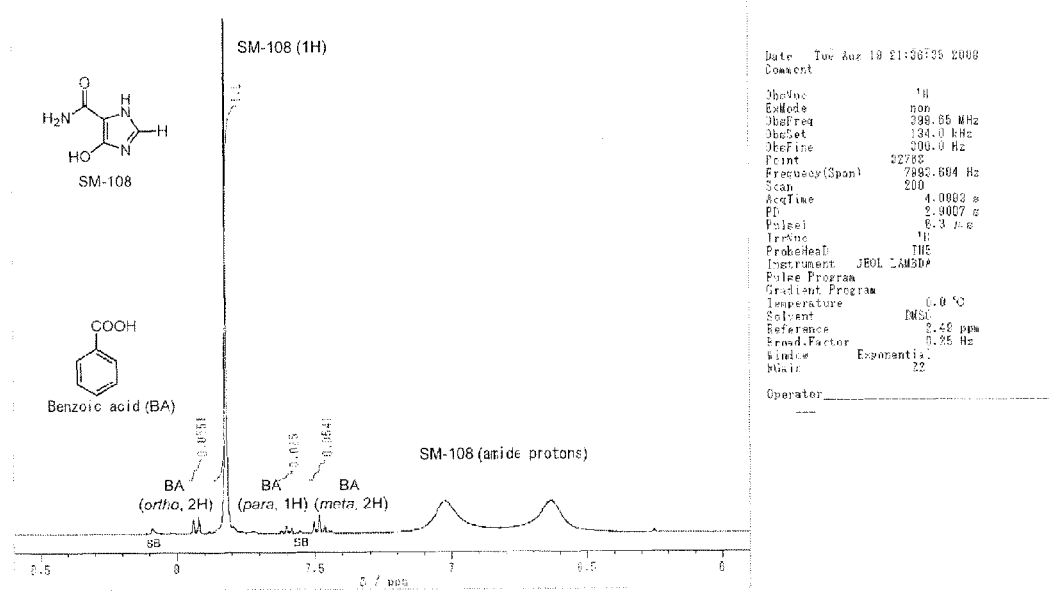
FIG. 3 shows an NMR spectrum of crystalline compound of SM-108.

Benzene sulfonic acid salt of SM-108 (99.5 mg) was dissolved in hot water (1 ml). The resulting solution was neutralized with 0.94 equivalent of sodium benzoate (48.1 mg). After stirring, the suspension was diluted with acetone (8 ml), and the crystals precipitated were collected by filtration. Crystals obtained were washed further with acetone and dried in vacuo to give SM-108 (40.4 mg; yield 89%) as colorless powders. Analysis by $^1$H-NMR showed that crystalline compound of SM-108 thus obtained included 2.5% of benzoic acid as shown in FIG. 3.

(Evaluation 1) Evaluation of the Storage Stability in Crystalline State by Visual Observation SM-108 [2] obtained in Example 1 and benzensulfonic acid salt of SM-108 [5] obtained in Example 2 were placed in an autoclave at 120° C. under a saturated vapor of water for 30 minutes.

With above treatment, SM-108 [2] turned indigo-blue, whereas benzensulfonic acid salt of SM-108 [5] dissolved partially but remained colorless and formed colorless crystals again by drying under reduced pressure.

(Evaluation 2) Evaluation of the Storage Stability in an Aqueous Solution

SM-108 obtained in Example 1 and hydrochloric acid salt of SM-108 obtained in Example 3 were dissolved into water to dilute aqueous solutions. UV-Vis spectra of those solutions were recorded just after making solutions and after leaving at room temperature for 60 days. In the case of an aqueous solution of SM-108, after 60 days, a broad absorption appeared in the visible-light region (FIG. 1). On the other hand, an aqueous solution of hydrochloric acid of SM-108 remained colorless even after 60 days and its absorption spectrum did not change at all.

Formulation Example 1

Orally Administrable Formulation

| | | |
|---|---|---|
| 1. | 4-Carbamoyl-5-hydroxyimidazole | 500 mg |
| 2. | Mannit | 400 mg |
| 3. | 10% Alpha-starch | 94 mg |
| 4. | Magnesium stearate | 6 mg |

Above 1 and 2 are mixed and granulized by the addition of 3. The granules thus obtained are passed through a sieve and dried. Then, the granules are passed through a No. 16-mesh sieve (B.B.) and the particles obtained are mixed with 4, and then formulated to 1000 mg of tablets by compression.

The invention claimed is:

1. A method for preparing an organic sulfonic acid salt of aminomalonamide by direct recrystallization performed in an alcoholic solvent with the addition of the organic sulfonic acid into a crude product obtained through the reaction of diethyl aminomalonate and ammonia in an organic solvent.

2. The method for preparation according to claim 1, wherein the organic solvent is an alcoholic solvent.

3. The method for preparation according to claim 2, wherein the alcoholic solvent is methylalcohol.

4. The method for preparation according to claim 1, wherein the organic sulfonic acid is an arylsulfonic acid.

5. The method for preparation according to claim 4, wherein the arylsulfonic acid is benzenesulfonic acid or toluenesulfonic acid.

6. A method for preparing an organic sulfonic acid salt of SM-108 characterized in obtaining the organic sulfonic acid salt of SM-108 precipitated out after an organic sulfonic acid salt of aminomalonamide is added to trialkoxymethine stirred in an organic solvent under heating.

7. The method for preparation according to claim 6, wherein the organic sulfonic acid is an arylsulfonic acid.

8. The method for preparation according to claim 7, wherein the arylsulfonic acid is benzenesulfonic acid or toluenesulfonic acid.

9. A method for preparing an organic sulfonic acid salt of SM-108 characterized in obtaining the organic sulfonic acid salt of SM-108 precipitated out after an organic sulfonic acid salt of aminomalonamide and trialkoxymethine are mixed in an organic solvent stirred under heating, wherein the organic sulfonic acid salt of aminomalonamide is obtained by the addition of ammonia and an organic sulfonic acid to an inorganic acid salt of diethyl aminomalonate stirred under heating in an organic solvent under atmosphere of an inert gas.

10. The method for preparing an organic sulfonic acid salt of SM-108 according to claim 9, wherein the organic sulfonic acid is an arylsulfonic acid.

11. The method for preparing an organic sulfonic acid salt of SM-108 according to claim 10, wherein the arylsulfonic acid is benzenesulfonic acid or toluenesulfonic acid.

12. A method for preparing a crystalline compound of SM-108 comprising collecting a crystalline of SM-108 precipitated out by dilution of an aqueous solution with a hydrophilic organic solvent, wherein the aqueous solution is obtained after neutralization of an organic sulfonic acid salt of SM-108 in an aqueous solution by the addition of an alkaline metallic salt of a benzenecarboxylic acid or an aqueous solution thereof, wherein an amount of 0.5 to 5% of the benzenecarboxylic acid remained after preparation of the crystalline compound of SM-108.

13. The method for preparation according to claim 12, wherein the alkaline metallic salt of a benzenecarboxylic acid is a sodium salt of a benzenecarboxylic acid.

14. The method for preparation according to claim 12, wherein the organic sulfonic acid is an arylsulfonic acid.

15. The method for preparation according to claim 14, wherein the arylsulfonic acid is benzenesulfonic acid or toluenesulfonic acid.

* * * * *